United States Patent [19]

Spence

[11] 4,226,232

[45] Oct. 7, 1980

[54] WOUND DRESSING

[75] Inventor: Wayman R. Spence, Waco, Tex.

[73] Assignee: Spenco Medical Corporation, Waco, Tex.

[21] Appl. No.: 28,610

[22] Filed: Apr. 9, 1979

[51] Int. Cl.³ .............................................. A61L 15/00
[52] U.S. Cl. ................................................. 128/156
[58] Field of Search ............................... 128/155–156, 128/284, 287, 285, 290 R, 296

[56] References Cited

U.S. PATENT DOCUMENTS

| | | | |
|---|---|---|---|
| 3,386,441 | 6/1968 | DeMerre | 128/285 |
| 3,521,637 | 7/1970 | Waterbury | 128/285 |
| 3,670,731 | 6/1972 | Harmon | 128/156 |
| 3,731,683 | 5/1973 | Zaffaroni | 128/156 |
| 3,937,223 | 2/1976 | Roth | 128/156 |
| 4,055,184 | 10/1977 | Karami | 128/284 |
| 4,058,124 | 11/1977 | Yen et al. | 128/284 |
| 4,069,177 | 1/1978 | Smith | 128/284 |
| 4,123,397 | 10/1978 | Jones | 128/284 |
| 4,155,893 | 5/1979 | Fujimoto et al. | 128/284 |

*Primary Examiner*—C. Fred Rosenbaum
*Attorney, Agent, or Firm*—Richards, Harris & Medlock

[57] ABSTRACT

Wound dressings having a water absorbent graft copolymer and water mixture are provided for direct application to the wound. The dressings may also be packaged in porous bags which may be directly applied to the wound. Additional components in the wound dressing may include local anesthetics, hormonal compounds, enzymes, antibacterial agents, antifungal agents or silicone compounds.

24 Claims, 3 Drawing Figures

WOUND DRESSING

BACKGROUND OF THE INVENTION

Secreting skin wounds, such as decubitus ulcers, venous stasis ulcers, infected traumatic wounds, open surgical wounds and burns have long been a medical problem to keep clean and dry. If blood, serum and purulent matter are allowed to accumulate in the craters and crevices of these wounds, bacterial growth and crusted organic matter will promote infection and delay healing. In addition, secreting skin wounds may lead to anemia, infections, shock and even death through the loss of body proteins, electrolytes, fluids and heat.

Methods used in the past to cover and protect secreting skin wounds have consisted of gauze dressings, nonwoven fabrics, and a variety of other cellulose and synthetic products. Enzyme preparations and other chemical agents have also been used to digest organic secretions from skin ulcers. More recently, spherical hydrophilic beads of dextronomers have been utilized to absorb secretions from skin ulcers. However, all of these approaches have shortcomings related to absorption capacities, wound cleaning, body movement, expense and effectiveness.

Therefore, a need has arisen for a wound dressing for providing an elastic barrier between the body's internal environment and the external environment. A need has also arisen for a wound dressing which would in itself absorb large quantities of blood, serum and pus, separate these secretions from subcutaneous tissues, provide a heat transmission barrier between the body and the external environment, provide at least a partial barrier to loss of body fluids and electrolytes, provide some relief from pain, prevent drying of denuded subcutanaceous tissues, allow for body movement without breakage of the barrier between the wound and external environment and be reasonably economical in cost.

SUMMARY OF THE INVENTION

The present invention provides a wound dressing which is capable of absorbing large quantities of blood, serum and pus. The wound dressing provided by the invention is able to separate these secretions from subcutanaceous tissues and provide a heat tranmission barrier between the body and the external environment. Further, another aspect of this invention relates to a wound dressing which provides a partial barrier to the loss of body fluids and electrolytes, reduces pain and prevents drying of denuded subcutanaceous tissues. Another aspect of the invention relates to a wound dressing which does not adhere to the body or wound and allows for hydrotherapy cleansing. Still another aspect of the invention relates to a wound dressing which is capable of conforming to the configuration of the wound while allowing for body movement without breakage of the barrier between the body and the external environment provided by the wound dressing. Another aspect of the invention relates to wound dressings which are easy to apply and economical in cost. Further, another aspect of the invention relates to a wound dressing which is able to contain an effective therapeutic amount of a physiologically active component.

The wound dressing of the present invention comprises a mixture that includes a water absorbent graft copolymer and water. The mixture may also include optional components such as enzymes, local anesthetics, hormonal compounds, antibacterial agents and antifungal agents. Preferably, water is present in the mixture of an amount of from about 10% to about 50% of the graft copolymer's water absorbency.

The method according to the invention comprises applying to the wound a mixture of a water absorbent graft copolymer and water. In one embodiment, the mixture may be contained within a water permeable porous bag.

BRIEF DESCRIPTION OF THE DRAWINGS

A more complete understanding of the invention may be had by reference to the following detailed description when taken in conjunction with the accompanying drawings wherein.

DETAILED DESCRIPTION OF THE INVENTION

Figure 1:
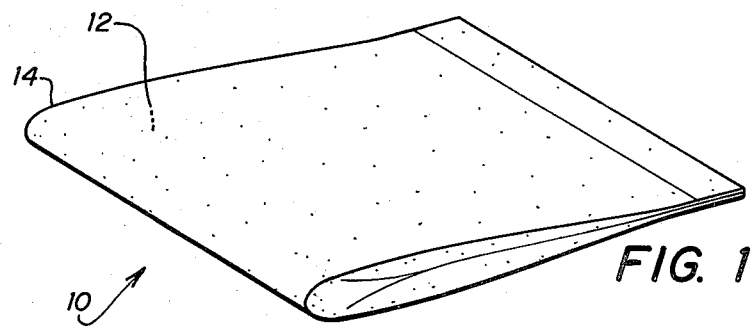
FIG. 1 is a perspective view of a bandage incorporating the wound dressing according to the invention.

According to the invention, a wound dressing is provided that has the capacity to absorb several times its own weight of water soluble fluids, such as serum, blood or pus. The wound dressing according to the invention also provides a partial barrier to loss of body fluids and electrolytes and allows for body movement without breakage of the seal created by the wound dressing between the wound and the external environment. Other advantages and benefits from the invention will be hereinafter described.

According to the invention, a wound dressing is provided for direct application to a wound that comprises a mixture of a water absorbent graft copolymer and water. The preferred type of water absorbent graft copolymer is a hydrolyzed starch-polyacrylonitrile copolymer. Hydrolyzed starch-polyacrylonitrile graft copolymers exhibiting the capacity to absorb from about 300 to about 1,000 times their weight of deionized water are known at this time.

The hydrolyzed starch-polyacrylonitrile graft copolymers may be produced by exposure of starch, either gelatinized or ungelatinized, to cerium salt, such as cerium ammonium nitrate, which acts as a catalyst to generate free radicals. Polyacrylonitrile chains form at the site of these free radicals. The resulting material is then saponified in alkali such as sodium hydroxide to hydrolyze the polyacrylonitrile chains to carboxamide and alkali metal carboxylate groups mixed with metal salts. After drying, the material can absorb about 300 to 400 times its weight of deionized water. Drying can be accomplished by drum, tumble, air, vacuum drying or any other suitable method known to those skilled in the art. Extraction of the copolymer dispersion with alcohol before drying provides a material capable of absorbing about 800 to about 1,000 times its weight of deionized water. The fluid absorbency of the copolymer is determined by suspending a weighed amount of dry copolymer in an excess of deionized water and filtering the resulting solution to recover the unabsorbed fluid.

Prior to utilization of the copolymer according to the invention, the unreacted monomeric acrylonitrile is separated from the graft copolymer. Preferably, this is done prior to saponification. This can be accomplished by any method known to those skilled in the art, such as by steam distillation. The graft copolymer used in accordance with the invention must be nontoxic and physiologically acceptable. The water insoluble form of the hydrolyzed starch-polyacrylonitrile graft copolymer is used in accordance with the invention. Preferred hydrolyzed starch polyacrylonitrile graft copolymers for use in accordance with the invention and methods of manufacture are disclosed in U.S. Pat. No. 3,935,099 to Weaver, et al which is herein incorporated by reference. Such graft copolymers generally have molecular weights of about 50,000 to about 500,000. Unmodified corn starch is the preferred type of starch for use in synthesizing graft copolymers for use in accordance with the invention primarily because of low cost and availability.

The wound dressing of the present invention is prepared by mixing a quantity of water with a water absorbent graft copolymer to form a resulting gel mixture. Preferably, the mixture contains water in an amount from about 10% to about 50% of the graft copolymer's water absorbency. For example, if the graft copolymer is capable of absorbing about 300 times its weight of deionized water, the gel mixture comprising the wound dressing would preferably contain from about 30 grams to about 150 grams deionized water per gram of graft copolymer. The mixture of a water absorbent graft copolymer in water can be produced by mixing the two components by any method known to those skilled in the art. Preferably, the graft copolymer will be in flake or particle form prior to the addition of water to facilitate formation of the graft copolymer-water mixture. Most preferably, when used in particle form the graft copolymer for use in accordance with the invention has a particle size of about 20 to about 100 mesh. Particle sizes smaller than 100 mesh are generally difficult to contain and can cause "blocking" to occur, that is, a thin layer of the gel dressing adjacent the wound becomes saturated with fluid and prevents mass transfer from the wound to unsaturated portions of the gel dressing. Particle sizes larger than 20 mesh generally will be inefficient and absorb fluids too slowly.

The mixture formed from the water absorbent graft copolymer and water components is preferably a gel. The amount of water present in the mixture will determine whether the mixture is in gel form. Generally, water present in an amount of from about 10% to about 50% of the graft copolymer's water absorbency will result in a gel mixture. The gel mixture preferably has the capacity to absorb several times its own weight of additional water and has the consistency in feel of finely crushed ice. The gel is easily moldable and nonsticky thereby facilitating placement of the gel over the area to be treated.

Since the mixture containing the water absorbent graft copolymer in water contains less water than the graft copolymer is capable of absorbing, the wound dressing will exhibit further potential for imbibing water. When the wound dressing according to the invention is placed in contact with a secreting skin wound, the imbibing forces of the wound dressing create a suction which immediately draws the surrounding water soluble secretions from the wound into the mixture.

While the absorption-gel wound dressing significantly improves wound cleanliness and reduces accumulations of necrotic, dried secretions, in the depths of wounds and skin ulcers, the wound dressing is not a substitute for surgical debridement when required. If necrotic tissue is already present and eschar formation has already occurred, debridement with a scalpal or scissors is necessary for the full potential of the absorption-gel wound dressing to be realized, since the absorption-gel wound dressing is primarily effective in removing water soluble secretions.

The wound dressing according to the invention may further comprise physiologically active components present in therapeutic amounts. For example, the wound dressing of the present invention may contain local anesthetics, hormonal compounds, enzymes, antibacterial agents, antifungal agents and lubricating and barrier chemicals such as silicone compounds, for example. Thus, the wound dressing according to the invention may also function as a vehicle for application of physiologically active components.

The wound dressing according to the invention may be placed in direct contact with a wound. The dressing may be lightly packed over a wound and held in place by a gauge dressing, for example. In another embodiment, the wound dressing can be contained within a sealed, porous, water and blood permeable bag. Thus, mass transfer readily occurs through the permeable paper to the inside of the bag and the absorption-gel wound dressing contained therein imbibes fluids from the wound. The long fiber paper will then hold the fluid swollen absorption-gel wound dressing internally, as the particle size is too large to pass through the paper. Once imbibed into the absorption-gel wound dressing contained within the bag, secretions such as blood or serum will not leak out of the bag. The bags containing the absorption-gel wound dressing bags can be used directly over wounds or packed into deep wounds and lightly covered with gauze dressings.

Referring now to the drawings, and particularly to FIG. 1, there is shown a bandage 10 comprising an absorption-gel wound dressing 12 contained within a bag 14. While bag 14 is shown in rectangular form it is to be understood that any desired shape may be employed. The material of bag 14 may be any porous, nontoxic, water permeable material. Preferably, the material of bag 14 is inert although physiologically active components may be contained therein. The preferred material of bag 14 is long fiber, wet strength treated paper. For example, one such paper which is suitable for use in constructing bag 14 is sold by the Schweitzer Division of the Kimberly-Clark Corporation under the trade name Berkshire Heat Sealed Tea Bag Paper which contains fibers which are spun from a solution of copolymerized vinyl chloride and vinyl acetate having the trade designation of "Vinyon". Preferably, the material has a porous permeability of about 230 cfm/ft$^2$ at a pressure of 0.5 inches of water.

Figure 2:
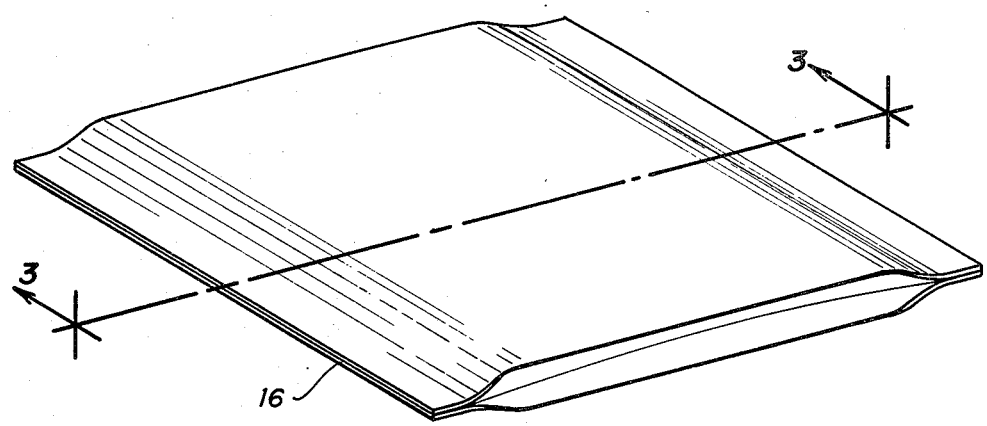
FIG. 2 is a perspective view showing the bandage of FIG. 1 packaged in an airtight package.
Figure 3:
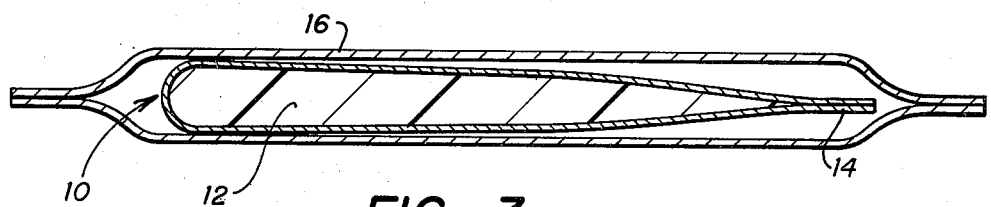
FIG. 3 is a sectional view of the packaged bandage taken along lines 3—3 in FIG. 2.

Preferably the wound dressings of the invention will be formulated and packaged prior to use. FIG. 2 illustrates bag 14 containing absorption-gel wound dressing 12 enclosed within an airtight bag 16. Airtight bag 16 prevents any evaporation or other loss of material from bag 14. Preferably airtight bag 16 will be constructed of aluminum foil or an aluminum sheet polymer laminate, or a polymer such as polyethylene. Airtight bag 16 may also be used to contain the wound dressing according to the invention without bag 14. FIG. 3 illustrates a sectional view of the packaged bandage along lines 3—3 of FIG. 2. Bandage 10 may be removed from airtight bag 16 merely by tearing or otherwise opening airtight bag 16.

To initially evaluate the clinical effectiveness of the absorption wound dressing, work was done by veterinarians on approximately 40 skin ulcers in dogs and horses using a graft copolymer made in accordance with U.S. Pat. No. 3,935,099 to Weaver, et al. These were pressure sores or traumatic wounds and provided an excellent medium to test applicability and biological efficiency of the absorption-gel wound dressing. Over a series of 4 months, the material proved to be an excellent method for cleaning these animal wounds, and no local or systemic toxicity was noted.

Clinical trials were conducted with a series of 25 human patients. These patients all suffered from decubitus ulcers or stasis ulcers. Their general care was supervised by several physicians and nurses, and a single nurse supervised the applications of the absorption-gel wound dressing to their skin ulcers. All patients previously had their skin ulcers treated with at least one medicinal preparation, but all patients were felt to be making less than optimal progress in healing.

Two different techniques were utilized for applying the absorption-gel wound dressing to skin ulcers. In the first technique, the absorption-gel wound dressing was lightly packed directly over the skin ulcer, covering the wound to a depth of approximately one centimeter. The absorption-gel wound dressing was then covered with a light gauze dressing, to hold the gel in place. In the second technique, the absorption-gel wound dressing was sealed inside a porous, permeable paper bag as previously described.

All skin ulcers treated in this study responded favorably to the use of absorption-gel wound dressing materials. The wounds either healed completely or developed a cleaner bed of granulation tissue. In every case the nursing and medical staff responsible for the clinical trials felt that skin ulcers treated with the absorption-gel wound dressing remained significantly cleaner, showed less eschar formation, fewer infections and less odor than ulcers treated with dry gauze dressings, saline soaped gauze dressings, dextronomer beads and enzymatic ointments. Patients also noted a reduction in pain when their skin ulcers were covered with the absorption-gel wound dressing.

Although preferred embodiments of the invention have been described in the foregoing detailed description and illustrated in the accompanying drawings, it will be understood that the invention is not limited to the embodiments disclosed, and the invention is capable of numerous rearrangements, modifications and substitutions of components and elements without departing from the spirit of the invention.

I claim:

1. A method for treating a secreting skin wound comprising applying to the wound a gel mixture comprising a water absorbent graft copolymer and water.

2. The method as recited in claim 1 wherein said graft copolymer is a hydrolyzed starch-polyacrylonitrile graft copolymer.

3. The method as recited in claim 2 wherein said copolymer has a molecular weight from about 50,000 to about 500,000.

4. For the method as recited in claims 1, 2 or 3 wherein said mixture contains water in an amount from about 10% to about 50% of the graft copolymer's water absorbency.

5. The method as recited in claim 1, 2 or 3 further comprising packaging said mixture in a sealed pouch prior to application, said pouch being porous for allowing mass transfer between said wound and said mixture.

6. A method for treating a secreting skin wound comprising applying in intimate contact with the wound a gel mixture comprising a water absorbent graft copolymer and water wherein water is present in an amount of from about 10% to about 50% of the graft copolymer's water absorbency.

7. A gel wound dressing comprising:
(a) a water absorbent hydrolyzed starch-polyacrylonitrile graft copolymer;
(b) water in an amount from about 10% to about 50% of the graft copolymer's water absorbency.

8. The wound dressing as recited in claim 7 wherein said graft copolymer has a molecular weight of from about 50,000 to about 500,000.

9. The wound dressing as recited in claim 7 wherein said copolymer is synthesized with unmodified corn starch.

10. The wound dressing as recited in claim 7 wherein water is present in an amount from about 20% to about 40% of the graft copolymer's water absorbency.

11. The wound dressing as recited in claim 7 further comprising an effective therapeutic amount of a physiologically active component.

12. The wound dressing as recited in claim 11 wherein said physiologically active component is an enzyme.

13. The wound dressing as recited in claim 11 wherein said physiologically active component is an antibacterial agent.

14. The wound dressing as recited in claim 11 wherein said physiologically active component is an antifungal agent.

15. The wound dressing as recited in claim 11 wherein said physiologically active component is a local anesthetic.

16. The wound dressing as recited in claim 11 wherein said physiologically active component is a hormonal compound.

17. The wound dressing as recited in claim 7 further comprising a silicone compound.

18. The wound dressing as recited in claims 7, 8, 9, 10, 11, 12, 13, 14, 15, 16 or 17 wherein said dressing is enclosed within a porous bag, said bag constructed of material which is nontoxic and water permeable.

19. A bandage for direct application to a skin wound comprising:
(a) a gel mixture comprising a water absorbent graft copolymer and water; and
(b) a bag containing said mixture, which bag is nontoxic, porous and water and blood permeable.

20. The bandage as recited in claim 19 wherein said bag comprises long fiber paper.

21. The bandage as recited in claim 19 wherein said mixture contains water in an amount of from about 10% to about 50% of the graft copolymer's water absorbency.

22. The bandage as recited in claim 19 wherein said bag comprises a fiber spun from a solution of copolymerized vinyl chloride and vinyl acetate.

23. The bandage as recited in claim 22 wherein the material of said bag has a porous permeability of about 230 cfm/ft$^2$.

24. The bandage as recited in claims 19, 20, 21, 22 or 23 wherein said bandage is packaged in an airtight bag.

* * * * *